US008221319B2

(12) United States Patent
Lovejoy

(10) Patent No.: US 8,221,319 B2
(45) Date of Patent: Jul. 17, 2012

(54) MEDICAL DEVICE FOR ASSESSING INTRAVASCULAR BLOOD VOLUME AND TECHNIQUE FOR USING THE SAME

(75) Inventor: David Lovejoy, Thiensville, WI (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 488 days.

(21) Appl. No.: 12/411,014

(22) Filed: Mar. 25, 2009

(65) Prior Publication Data

US 2010/0249559 A1 Sep. 30, 2010

(51) Int. Cl.
*A61B 5/00* (2006.01)

(52) U.S. Cl. .... 600/364; 600/323; 600/500; 128/204.23

(58) Field of Classification Search .................. 600/364, 600/483, 529–543, 500; 128/202.23, 204.21–204.26; 604/66

See application file for complete search history.

(56) References Cited

U.S. PATENT DOCUMENTS

| | | | |
|---|---|---|---|
| 3,638,640 | A | 2/1972 | Shaw |
| 3,721,813 | A | 3/1973 | Condon et al. |
| 4,586,513 | A | 5/1986 | Hamaguri |
| 4,603,700 | A | 8/1986 | Nichols et al. |
| 4,621,643 | A | 11/1986 | New, Jr. et al. |
| 4,653,498 | A | 3/1987 | New, Jr. et al. |
| 4,685,464 | A | 8/1987 | Goldberger et al. |
| 4,694,833 | A | 9/1987 | Hamaguri |
| 4,697,593 | A | 10/1987 | Evans et al. |
| 4,700,708 | A | 10/1987 | New, Jr. et al. |
| 4,714,080 | A | 12/1987 | Edgar, Jr. et al. |
| 4,714,341 | A | 12/1987 | Hamaguri et al. |
| 4,759,369 | A | 7/1988 | Taylor |
| 4,770,179 | A | 9/1988 | New, Jr. et al. |
| 4,773,422 | A | 9/1988 | Isaacson et al. |
| 4,776,339 | A | 10/1988 | Schreiber |
| 4,781,195 | A | 11/1988 | Martin |
| 4,796,636 | A | 1/1989 | Branstetter et al. |
| 4,800,495 | A | 1/1989 | Smith |
| 4,800,885 | A | 1/1989 | Johnson |
| 4,802,486 | A | 2/1989 | Goodman et al. |
| 4,805,623 | A | 2/1989 | Jöbsis |
| 4,807,630 | A | 2/1989 | Malinouskas |
| 4,807,631 | A | 2/1989 | Hersh et al. |
| 4,819,646 | A | 4/1989 | Cheung et al. |
| 4,819,752 | A | 4/1989 | Zelin |

(Continued)

FOREIGN PATENT DOCUMENTS

EP 0615723 9/1994

(Continued)

OTHER PUBLICATIONS

M Shamir, L A Eidelman, Y Floman, L Kaplan and R Pizov. Pulse oximetry plethysmographic waveform during changes in blood volume.(1999) Br. J. Anaesth. 82 (2): 178-181.*

(Continued)

*Primary Examiner* — Charles A Marmor, II
*Assistant Examiner* — Sunita Reddy

(57) ABSTRACT

Embodiments of the present invention relate to a system and method for determining a physiologic parameter of a patient. Specifically, embodiments of the present invention include methods and systems for correcting a pulse oximetry plethysmographic waveform variability measurement based on parameters that may influence the waveform variability. The corrected measurement may be used to estimate intravascular blood volume and/or fluid responsiveness of a patient.

18 Claims, 5 Drawing Sheets

64

OBTAIN PLETHYSMOGRAPHIC WAVEFORM SIGNAL FROM PATIENT — 66

OBTAIN DATA RELATING TO ONE OR MORE PATIENT PARAMETERS — 68

DETERMINE AN ADJUSTED PLETHYSMOGRAPHIC WAVEFORM VARIABILITY BASED ON THE PLETHYSMOGRAPHIC WAVEFORM SIGNAL AND THE DATA — 70

PROVIDE AN INDICATION OF THE ADJUSTED PLETHYSMOGRAPHIC WAVEFORM VARIABILITY — 72

U.S. PATENT DOCUMENTS 4,824,242 A 4/1989 Frick et al.
4,825,872 A 5/1989 Tan et al.
4,825,879 A 5/1989 Tan et al.
4,830,014 A 5/1989 Goodman et al.
4,832,484 A 5/1989 Aoyagi et al.
4,846,183 A 7/1989 Martin
4,848,901 A 7/1989 Hood, Jr.
4,854,699 A 8/1989 Edgar, Jr.
4,859,056 A 8/1989 Prosser et al.
4,859,057 A 8/1989 Taylor et al.
4,863,265 A 9/1989 Flower et al.
4,865,038 A 9/1989 Rich et al.
4,867,557 A 9/1989 Takatani et al.
4,869,253 A 9/1989 Craig, Jr. et al.
4,869,254 A 9/1989 Stone et al.
4,880,304 A 11/1989 Jaeb et al.
4,883,055 A 11/1989 Merrick
4,883,353 A 11/1989 Hansman et al.
4,890,619 A 1/1990 Hatschek
4,892,101 A 1/1990 Cheung et al.
4,901,238 A 2/1990 Suzuki et al.
4,908,762 A 3/1990 Suzuki et al.
4,911,167 A 3/1990 Corenman et al.
4,913,150 A 4/1990 Cheung et al.
4,926,867 A 5/1990 Kanda et al.
4,927,264 A 5/1990 Shiga et al.
4,928,692 A 5/1990 Goodman et al.
4,934,372 A 6/1990 Corenman et al.
4,936,679 A 6/1990 Mersch
4,938,218 A 7/1990 Goodman et al.
4,942,877 A 7/1990 Sakai et al.
4,948,248 A 8/1990 Lehman
4,955,379 A 9/1990 Hall
4,960,126 A 10/1990 Conlon et al.
4,964,408 A 10/1990 Hink et al.
4,971,062 A 11/1990 Hasebe et al.
4,972,331 A 11/1990 Chance
4,974,591 A 12/1990 Awazu et al.
5,007,423 A 4/1991 Branstetter et al.
5,025,791 A 6/1991 Niwa
RE33,643 E 7/1991 Isaacson et al.
5,028,787 A 7/1991 Rosenthal et al.
5,040,539 A 8/1991 Schmitt et al.
5,054,488 A 10/1991 Muz
5,055,671 A 10/1991 Jones
5,058,588 A 10/1991 Kaestle
5,065,749 A 11/1991 Hasebe et al.
5,066,859 A 11/1991 Karkar et al.
5,069,213 A 12/1991 Polczynski
5,078,136 A 1/1992 Stone et al.
5,084,327 A 1/1992 Stengel
5,088,493 A 2/1992 Giannini et al.
5,090,410 A 2/1992 Saper et al.
5,094,239 A 3/1992 Jaeb et al.
5,094,240 A 3/1992 Muz
5,099,841 A 3/1992 Heinonen et al.
5,099,842 A 3/1992 Mannheimer et al.
H1039 H 4/1992 Tripp et al.
5,104,623 A 4/1992 Miller
5,109,849 A 5/1992 Goodman et al.
5,111,817 A 5/1992 Clark et al.
5,113,861 A 5/1992 Rother
5,119,815 A 6/1992 Chance
5,122,974 A 6/1992 Chance
5,125,403 A 6/1992 Culp
5,127,406 A 7/1992 Yamaguchi
5,131,391 A 7/1992 Sakai et al.
5,140,989 A 8/1992 Lewis et al.
5,152,296 A 10/1992 Simons
5,154,175 A 10/1992 Gunther
5,158,082 A 10/1992 Jones
5,167,230 A 12/1992 Chance
5,170,786 A 12/1992 Thomas et al.
5,188,108 A 2/1993 Secker et al.
5,190,038 A 3/1993 Polson et al.
5,193,542 A 3/1993 Missanelli et al.
5,193,543 A 3/1993 Yelderman
5,203,329 A 4/1993 Takatani et al.
5,209,230 A 5/1993 Swedlow et al.
5,213,099 A 5/1993 Tripp et al.
5,216,598 A 6/1993 Branstetter et al.
5,217,012 A 6/1993 Young et al.
5,217,013 A 6/1993 Lewis et al.
5,218,962 A 6/1993 Mannheimer et al.
5,224,478 A 7/1993 Sakai et al.
5,226,417 A 7/1993 Swedlow et al.
5,228,440 A 7/1993 Chung et al.
5,237,994 A 8/1993 Goldberger
5,239,185 A 8/1993 Ito et al.
5,246,002 A 9/1993 Prosser
5,246,003 A 9/1993 DeLonzor
5,247,931 A 9/1993 Norwood
5,247,932 A 9/1993 Chung et al.
5,249,576 A 10/1993 Goldberger et al.
5,253,645 A 10/1993 Friedman et al.
5,253,646 A 10/1993 Delpy et al.
5,259,381 A 11/1993 Cheung et al.
5,259,761 A 11/1993 Schnettler et al.
5,263,244 A 11/1993 Centa et al.
5,267,562 A 12/1993 Ukawa et al.
5,267,563 A 12/1993 Swedlow et al.
5,273,036 A 12/1993 Kronberg et al.
5,275,159 A 1/1994 Griebel
5,279,295 A 1/1994 Martens et al.
5,285,783 A 2/1994 Secker
5,285,784 A 2/1994 Seeker
5,287,853 A 2/1994 Vester et al.
5,291,884 A 3/1994 Heinemann et al.
5,297,548 A 3/1994 Pologe
5,299,120 A 3/1994 Kaestle
5,299,570 A 4/1994 Hatschek
5,309,908 A 5/1994 Friedman et al.
5,311,865 A 5/1994 Mayeux
5,313,940 A 5/1994 Fuse et al.
5,323,776 A 6/1994 Blakeley et al.
5,329,922 A 7/1994 Atlee, III
5,337,744 A 8/1994 Branigan
5,339,810 A 8/1994 Ivers et al.
5,343,818 A 9/1994 McCarthy et al.
5,343,869 A 9/1994 Pross et al.
5,348,003 A 9/1994 Caro
5,348,004 A 9/1994 Hollub et al.
5,349,519 A 9/1994 Kaestle
5,349,952 A 9/1994 McCarthy et al.
5,349,953 A 9/1994 McCarthy et al.
5,351,685 A 10/1994 Potratz
5,353,799 A 10/1994 Chance
5,355,880 A 10/1994 Thomas et al.
5,355,882 A 10/1994 Ukawa et al.
5,361,758 A 11/1994 Hall et al.
5,365,066 A 11/1994 Krueger, Jr. et al.
5,368,025 A 11/1994 Young et al.
5,368,026 A 11/1994 Swedlow et al.
5,368,224 A 11/1994 Richardson et al.
5,372,136 A 12/1994 Steuer et al.
5,377,675 A 1/1995 Ruskewicz et al.
5,385,143 A 1/1995 Aoyagi
5,387,122 A 2/1995 Goldberger et al.
5,390,670 A 2/1995 Centa et al.
5,392,777 A 2/1995 Swedlow et al.
5,398,680 A 3/1995 Polson et al.
5,402,777 A 4/1995 Warring et al.
5,411,023 A 5/1995 Morris, Sr. et al.
5,411,024 A 5/1995 Thomas et al.
5,413,099 A 5/1995 Schmidt et al.
5,413,100 A 5/1995 Barthelemy et al.
5,413,101 A 5/1995 Sugiura
5,413,102 A 5/1995 Schmidt et al.
5,417,207 A 5/1995 Young et al.
5,421,329 A 6/1995 Casciani et al.
5,425,360 A 6/1995 Nelson
5,425,362 A 6/1995 Siker et al.
5,427,093 A 6/1995 Ogawa et al.
5,429,128 A 7/1995 Cadell et al.
5,429,129 A 7/1995 Lovejoy et al.
5,431,159 A 7/1995 Baker et al.
5,431,170 A 7/1995 Mathews 5,437,275 A 8/1995 Amundsen et al.
5,438,986 A 8/1995 Disch et al.
5,448,991 A 9/1995 Polson et al.
5,452,717 A 9/1995 Branigan et al.
5,465,714 A 11/1995 Scheuing
5,469,845 A 11/1995 DeLonzor et al.
RE35,122 E 12/1995 Corenman et al.
5,482,034 A 1/1996 Lewis et al.
5,482,036 A 1/1996 Diab et al.
5,483,646 A 1/1996 Uchikoga
5,485,847 A 1/1996 Baker, Jr.
5,490,505 A 2/1996 Diab et al.
5,490,523 A 2/1996 Isaacson et al.
5,491,299 A 2/1996 Naylor et al.
5,494,032 A 2/1996 Robinson et al.
5,497,771 A 3/1996 Rosenheimer
5,499,627 A 3/1996 Steuer et al.
5,503,148 A 4/1996 Pologe et al.
5,505,199 A 4/1996 Kim
5,507,286 A 4/1996 Solenberger
5,517,988 A 5/1996 Gerhard
5,520,177 A 5/1996 Ogawa et al.
5,521,851 A 5/1996 Wei et al.
5,522,388 A 6/1996 Ishikawa et al.
5,524,617 A 6/1996 Mannheimer
5,529,064 A 6/1996 Rall et al.
5,533,507 A 7/1996 Potratz et al.
5,551,423 A 9/1996 Sugiura
5,551,424 A 9/1996 Morrison et al.
5,553,614 A 9/1996 Chance
5,553,615 A 9/1996 Carim et al.
5,555,882 A 9/1996 Richardson et al.
5,558,096 A 9/1996 Palatnik
5,560,355 A 10/1996 Merchant et al.
5,564,417 A 10/1996 Chance
5,575,284 A 11/1996 Athan et al.
5,575,285 A 11/1996 Takanashi et al.
5,577,500 A 11/1996 Potratz
5,582,169 A 12/1996 Oda et al.
5,584,296 A 12/1996 Cui et al.
5,588,425 A 12/1996 Sackner et al.
5,588,427 A 12/1996 Tien
5,590,652 A 1/1997 Inai
5,595,176 A 1/1997 Yamaura
5,596,986 A 1/1997 Goldfarb
5,611,337 A 3/1997 Bukta
5,617,852 A 4/1997 MacGregor
5,619,992 A 4/1997 Guthrie et al.
5,626,140 A 5/1997 Feldman et al.
5,630,413 A 5/1997 Thomas et al.
5,632,272 A 5/1997 Diab et al.
5,632,273 A 5/1997 Suzuki
5,634,459 A 6/1997 Gardosi
5,634,461 A * 6/1997 Faithfull et al. ............... 600/483
5,638,593 A 6/1997 Gerhardt et al.
5,638,818 A 6/1997 Diab et al.
5,645,059 A 7/1997 Fein et al.
5,645,060 A 7/1997 Yorkey
5,645,440 A 7/1997 Tobler et al.
5,660,567 A 8/1997 Nierlich et al.
5,662,105 A 9/1997 Tien
5,662,106 A 9/1997 Swedlow et al.
5,666,952 A 9/1997 Fuse et al.
5,671,529 A 9/1997 Nelson
5,673,692 A 10/1997 Schulze et al.
5,673,693 A 10/1997 Solenberger
5,676,139 A 10/1997 Goldberger et al.
5,676,141 A 10/1997 Hollub
5,678,544 A 10/1997 DeLonzor et al.
5,680,857 A 10/1997 Pelikan et al.
5,685,299 A 11/1997 Diab et al.
5,685,301 A 11/1997 Klomhaus
5,687,719 A 11/1997 Sato et al.
5,687,722 A 11/1997 Tien et al.
5,692,503 A 12/1997 Keunstner
5,692,505 A 12/1997 Fouts
5,709,205 A 1/1998 Bukta
5,713,355 A 2/1998 Richardson et al.
5,724,967 A 3/1998 Venkatachalam
5,727,547 A 3/1998 Levinson et al.
5,730,124 A 3/1998 Yamauchi
5,731,582 A 3/1998 West
D393,830 S 4/1998 Tobler et al.
5,743,260 A 4/1998 Chung et al.
5,743,263 A 4/1998 Baker, Jr.
5,746,206 A 5/1998 Mannheimer
5,746,697 A 5/1998 Swedlow et al.
5,752,914 A 5/1998 DeLonzor et al.
5,755,226 A 5/1998 Carim et al.
5,758,644 A 6/1998 Diab et al.
5,760,910 A 6/1998 Lepper, Jr. et al.
5,766,125 A 6/1998 Aoyagi et al.
5,766,127 A 6/1998 Pologe et al.
5,769,785 A 6/1998 Diab et al.
5,772,587 A 6/1998 Gratton et al.
5,774,213 A 6/1998 Trebino et al.
5,776,058 A 7/1998 Levinson et al.
5,776,059 A 7/1998 Kaestle
5,779,630 A 7/1998 Fein et al.
5,779,631 A 7/1998 Chance
5,782,237 A 7/1998 Casciani et al.
5,782,756 A 7/1998 Mannheimer
5,782,758 A 7/1998 Ausec et al.
5,786,592 A 7/1998 Hök
5,790,729 A 8/1998 Pologe et al.
5,792,052 A 8/1998 Isaacson et al.
5,795,292 A 8/1998 Lewis et al.
5,797,841 A 8/1998 DeLonzor et al.
5,800,348 A 9/1998 Kaestle
5,800,349 A 9/1998 Isaacson et al.
5,803,910 A 9/1998 Potratz
5,807,246 A 9/1998 Sakaguchi et al.
5,807,247 A 9/1998 Merchant et al.
5,807,248 A 9/1998 Mills
5,810,723 A 9/1998 Aldrich
5,810,724 A 9/1998 Gronvall
5,813,980 A 9/1998 Levinson et al.
5,817,008 A 10/1998 Rafert et al.
5,817,009 A 10/1998 Rosenheimer et al.
5,817,010 A 10/1998 Hibl
5,818,985 A 10/1998 Merchant et al.
5,820,550 A 10/1998 Polson et al.
5,823,950 A 10/1998 Diab et al.
5,823,952 A 10/1998 Levinson et al.
5,827,182 A 10/1998 Raley et al.
5,830,135 A 11/1998 Bosque et al.
5,830,136 A 11/1998 DeLonzor et al.
5,830,137 A 11/1998 Scharf
5,830,139 A 11/1998 Abreu
5,839,439 A 11/1998 Nierlich et al.
RE36,000 E 12/1998 Swedlow et al.
5,842,979 A 12/1998 Jarman et al.
5,842,981 A 12/1998 Larsen et al.
5,842,982 A 12/1998 Mannheimer
5,846,190 A 12/1998 Woehrle
5,851,178 A 12/1998 Aronow
5,851,179 A 12/1998 Ritson et al.
5,853,364 A 12/1998 Baker, Jr. et al.
5,860,919 A 1/1999 Kiani-Azarbayjany et al.
5,865,736 A 2/1999 Baker, Jr. et al.
5,871,442 A 2/1999 Madarasz et al.
5,873,821 A 2/1999 Chance et al.
5,879,294 A 3/1999 Anderson et al.
5,885,213 A 3/1999 Richardson et al.
5,890,929 A 4/1999 Mills et al.
5,891,021 A 4/1999 Dillon et al.
5,891,022 A 4/1999 Pologe
5,891,024 A 4/1999 Jarman et al.
5,891,025 A 4/1999 Buschmann et al.
5,891,026 A 4/1999 Wang et al.
5,902,235 A 5/1999 Lewis et al.
5,910,108 A 6/1999 Solenberger
5,911,690 A 6/1999 Rall
5,912,656 A 6/1999 Tham et al.
5,913,819 A 6/1999 Taylor et al.
5,916,154 A 6/1999 Hobbs et al.
5,916,155 A 6/1999 Levinson et al.
5,919,133 A 7/1999 Taylor et al.

| | | | |
|---|---|---|---|
| 5,919,134 | A | 7/1999 | Diab |
| 5,920,263 | A | 7/1999 | Huttenhoff et al. |
| 5,921,921 | A | 7/1999 | Potratz et al. |
| 5,922,607 | A | 7/1999 | Bernreuter |
| 5,924,979 | A | 7/1999 | Swedlow et al. |
| 5,924,980 | A | 7/1999 | Coetzee |
| 5,924,982 | A | 7/1999 | Chin |
| 5,924,985 | A | 7/1999 | Jones |
| 5,934,277 | A | 8/1999 | Mortz |
| 5,934,925 | A | 8/1999 | Tobler et al. |
| 5,940,182 | A | 8/1999 | Lepper, Jr. et al. |
| 5,954,644 | A | 9/1999 | Dettling et al. |
| 5,960,610 | A | 10/1999 | Levinson et al. |
| 5,961,450 | A | 10/1999 | Merchant et al. |
| 5,961,452 | A | 10/1999 | Chung et al. |
| 5,964,701 | A | 10/1999 | Asada et al. |
| 5,971,930 | A | 10/1999 | Elghazzawi |
| 5,978,691 | A | 11/1999 | Mills |
| 5,978,693 | A | 11/1999 | Hamilton et al. |
| 5,983,122 | A | 11/1999 | Jarman et al. |
| 5,987,343 | A | 11/1999 | Kinast |
| 5,991,648 | A | 11/1999 | Levin |
| 5,995,855 | A | 11/1999 | Kiani et al. |
| 5,995,856 | A | 11/1999 | Mannheimer et al. |
| 5,995,858 | A | 11/1999 | Kinast |
| 5,995,859 | A | 11/1999 | Takahashi |
| 5,997,343 | A | 12/1999 | Mills et al. |
| 5,999,834 | A | 12/1999 | Wang et al. |
| 6,002,952 | A | 12/1999 | Diab et al. |
| 6,005,658 | A | 12/1999 | Kaluza et al. |
| 6,006,120 | A | 12/1999 | Levin |
| 6,011,985 | A | 1/2000 | Athan et al. |
| 6,011,986 | A | 1/2000 | Diab et al. |
| 6,014,576 | A | 1/2000 | Raley et al. |
| 6,018,673 | A | 1/2000 | Chin et al. |
| 6,018,674 | A | 1/2000 | Aronow |
| 6,022,321 | A | 2/2000 | Amano et al. |
| 6,023,541 | A | 2/2000 | Merchant et al. |
| 6,026,312 | A | 2/2000 | Shemwell et al. |
| 6,026,314 | A | 2/2000 | Amerov et al. |
| 6,031,603 | A | 2/2000 | Fine et al. |
| 6,035,223 | A | 3/2000 | Baker, Jr. |
| 6,036,642 | A | 3/2000 | Diab et al. |
| 6,041,247 | A | 3/2000 | Weckstrom et al. |
| 6,044,283 | A | 3/2000 | Fein et al. |
| 6,047,201 | A | 4/2000 | Jackson, III |
| 6,061,584 | A | 5/2000 | Lovejoy et al. |
| 6,064,898 | A | 5/2000 | Aldrich |
| 6,064,899 | A | 5/2000 | Fein et al. |
| 6,067,462 | A | 5/2000 | Diab et al. |
| 6,073,038 | A | 6/2000 | Wang et al. |
| 6,078,833 | A | 6/2000 | Hueber |
| 6,081,735 | A | 6/2000 | Diab et al. |
| 6,081,742 | A | 6/2000 | Amano et al. |
| 6,083,157 | A | 7/2000 | Noller |
| 6,083,172 | A | 7/2000 | Baker, Jr. et al. |
| 6,088,607 | A * | 7/2000 | Diab et al. .................... 600/322 |
| 6,094,592 | A | 7/2000 | Yorkey et al. |
| 6,095,974 | A | 8/2000 | Shemwell et al. |
| 6,099,481 | A | 8/2000 | Daniels et al. |
| 6,104,938 | A | 8/2000 | Huiku et al. |
| 6,112,107 | A | 8/2000 | Hannula |
| 6,113,541 | A | 9/2000 | Dias et al. |
| 6,115,621 | A | 9/2000 | Chin |
| 6,120,460 | A | 9/2000 | Abreu |
| 6,122,535 | A | 9/2000 | Kaestle et al. |
| 6,133,994 | A | 10/2000 | Mathews et al. |
| 6,134,460 | A | 10/2000 | Chance |
| 6,135,952 | A | 10/2000 | Coetzee |
| 6,144,444 | A | 11/2000 | Haworth et al. |
| 6,144,867 | A | 11/2000 | Walker et al. |
| 6,144,868 | A | 11/2000 | Parker |
| 6,149,481 | A | 11/2000 | Wang et al. |
| 6,150,951 | A | 11/2000 | Olejniczak |
| 6,151,107 | A | 11/2000 | Schöllermann et al. |
| 6,151,518 | A | 11/2000 | Hayashi |
| 6,152,754 | A | 11/2000 | Gerhardt et al. |
| 6,154,667 | A | 11/2000 | Miura et al. |
| 6,157,850 | A | 12/2000 | Diab et al. |
| 6,163,715 | A | 12/2000 | Larsen et al. |
| 6,165,005 | A | 12/2000 | Mills et al. |
| 6,173,196 | B1 | 1/2001 | Delonzor et al. |
| 6,178,343 | B1 | 1/2001 | Bindszus et al. |
| 6,181,958 | B1 | 1/2001 | Steuer et al. |
| 6,181,959 | B1 | 1/2001 | Schöllermann et al. |
| 6,184,521 | B1 | 2/2001 | Coffin, IV et al. |
| 6,188,470 | B1 | 2/2001 | Grace |
| 6,192,260 | B1 | 2/2001 | Chance |
| 6,195,575 | B1 | 2/2001 | Levinson |
| 6,198,951 | B1 | 3/2001 | Kosuda et al. |
| 6,206,830 | B1 | 3/2001 | Diab et al. |
| 6,213,952 | B1 | 4/2001 | Finarov et al. |
| 6,217,523 | B1 | 4/2001 | Amano et al. |
| 6,222,189 | B1 | 4/2001 | Misner et al. |
| 6,226,539 | B1 | 5/2001 | Potratz |
| 6,226,540 | B1 | 5/2001 | Bernreuter et al. |
| 6,229,856 | B1 | 5/2001 | Diab et al. |
| 6,230,035 | B1 | 5/2001 | Aoyagi et al. |
| 6,233,470 | B1 | 5/2001 | Tsuchiya |
| 6,236,871 | B1 | 5/2001 | Tsuchiya |
| 6,236,872 | B1 | 5/2001 | Diab et al. |
| 6,240,305 | B1 | 5/2001 | Tsuchiya |
| 6,253,097 | B1 | 6/2001 | Aronow et al. |
| 6,253,098 | B1 | 6/2001 | Walker et al. |
| 6,256,523 | B1 | 7/2001 | Diab et al. |
| 6,256,524 | B1 | 7/2001 | Walker et al. |
| 6,261,236 | B1 | 7/2001 | Grimblatov |
| 6,263,221 | B1 | 7/2001 | Chance et al. |
| 6,263,222 | B1 | 7/2001 | Diab et al. |
| 6,263,223 | B1 | 7/2001 | Sheperd et al. |
| 6,266,546 | B1 | 7/2001 | Steuer et al. |
| 6,266,547 | B1 | 7/2001 | Walker et al. |
| 6,272,363 | B1 | 8/2001 | Casciani et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,894 | B1 | 9/2001 | Oppelt et al. |
| 6,285,895 | B1 | 9/2001 | Ristolainen et al. |
| 6,285,896 | B1 | 9/2001 | Tobler et al. |
| 6,298,252 | B1 | 10/2001 | Kovach et al. |
| 6,308,089 | B1 | 10/2001 | Von der Ruhr et al. |
| 6,312,393 | B1 | 11/2001 | Abreu |
| 6,321,100 | B1 | 11/2001 | Parker |
| 6,330,468 | B1 | 12/2001 | Scharf |
| 6,334,065 | B1 | 12/2001 | Al-Ali et al. |
| 6,339,715 | B1 | 1/2002 | Bahr et al. |
| 6,343,223 | B1 | 1/2002 | Chin et al. |
| 6,343,224 | B1 | 1/2002 | Parker |
| 6,349,228 | B1 | 2/2002 | Kiani et al. |
| 6,351,658 | B1 | 2/2002 | Middleman et al. |
| 6,353,750 | B1 | 3/2002 | Kimura et al. |
| 6,356,774 | B1 | 3/2002 | Bernstein et al. |
| 6,360,113 | B1 | 3/2002 | Dettling |
| 6,360,114 | B1 | 3/2002 | Diab et al. |
| 6,361,501 | B1 | 3/2002 | Amano et al. |
| 6,363,269 | B1 | 3/2002 | Hanna et al. |
| 6,370,408 | B1 | 4/2002 | Merchant et al. |
| 6,370,409 | B1 | 4/2002 | Chung et al. |
| 6,374,129 | B1 | 4/2002 | Chin et al. |
| 6,377,829 | B1 | 4/2002 | Al-Ali et al. |
| 6,381,479 | B1 | 4/2002 | Norris |
| 6,381,480 | B1 | 4/2002 | Stoddart et al. |
| 6,385,471 | B1 | 5/2002 | Mortz |
| 6,385,821 | B1 | 5/2002 | Modgil et al. |
| 6,388,240 | B2 | 5/2002 | Schulz et al. |
| 6,393,310 | B1 | 5/2002 | Kuenster |
| 6,397,091 | B2 | 5/2002 | Diab et al. |
| 6,397,092 | B1 | 5/2002 | Norris et al. |
| 6,397,093 | B1 | 5/2002 | Aldrich |
| 6,400,971 | B1 | 6/2002 | Finarov et al. |
| 6,400,972 | B1 | 6/2002 | Fine |
| 6,402,690 | B1 | 6/2002 | Rhee et al. |
| 6,408,198 | B1 | 6/2002 | Hanna et al. |
| 6,411,832 | B1 | 6/2002 | Guthermann |
| 6,411,833 | B1 | 6/2002 | Baker, Jr. et al. |
| 6,415,236 | B2 | 7/2002 | Kobayashi et al. |
| 6,419,671 | B1 | 7/2002 | Lemberg |
| 6,421,549 | B1 | 7/2002 | Jacques |

6,430,423 B2 8/2002 DeLonzor et al.
6,430,513 B1 8/2002 Wang et al.
6,430,525 B1 8/2002 Weber et al.
6,434,408 B1 8/2002 Heckel et al.
6,438,399 B1 8/2002 Kurth
6,449,501 B1 9/2002 Reuss
6,453,183 B1 9/2002 Walker
6,453,184 B1 9/2002 Hyogo et al.
6,456,862 B2 9/2002 Benni
6,461,305 B1 10/2002 Schnall
6,463,310 B1 10/2002 Swedlow et al.
6,463,311 B1 10/2002 Diab
6,466,808 B1 10/2002 Chin et al.
6,466,809 B1 10/2002 Riley
6,470,199 B1 10/2002 Kopotic et al.
6,470,200 B2 10/2002 Walker et al.
6,480,729 B2 11/2002 Stone
6,487,439 B1 11/2002 Skladnev et al.
6,490,466 B1 12/2002 Fein et al.
6,496,711 B1 12/2002 Athan et al.
6,498,942 B1 12/2002 Esenaliev et al.
6,501,974 B2 12/2002 Huiku
6,501,975 B2 12/2002 Diab et al.
6,505,060 B1 1/2003 Norris
6,505,061 B2 1/2003 Larson
6,505,133 B1 1/2003 Hanna et al.
6,510,329 B2 1/2003 Heckel
6,510,331 B1 1/2003 Williams et al.
6,512,937 B2 1/2003 Blank et al.
6,515,273 B2 2/2003 Al-Ali
6,519,484 B1 2/2003 Lovejoy et al.
6,519,486 B1 2/2003 Edgar, Jr. et al.
6,519,487 B1 2/2003 Parker
6,525,386 B1 2/2003 Mills et al.
6,526,300 B1 2/2003 Kiani et al.
6,526,301 B2 2/2003 Larsen et al.
6,541,756 B2 4/2003 Schulz et al.
6,542,764 B1 4/2003 Al-Ali et al.
6,544,193 B2 4/2003 Abreu
6,546,267 B1 4/2003 Sugiura et al.
6,549,795 B1 4/2003 Chance
6,553,241 B2 4/2003 Mannheimer et al.
6,553,242 B1 4/2003 Sarussi
6,553,243 B2 4/2003 Gurley
6,556,852 B1 4/2003 Schulze et al.
6,560,470 B1 5/2003 Pologe
6,564,077 B2 5/2003 Mortara
6,564,088 B1 5/2003 Soller et al.
6,571,113 B1 5/2003 Fein et al.
6,571,114 B1 5/2003 Koike et al.
6,574,491 B2 6/2003 Elghazzawi
6,580,086 B1 6/2003 Schulz et al.
6,584,336 B1 6/2003 Ali et al.
6,587,703 B2 7/2003 Cheng et al.
6,587,704 B1 7/2003 Fine et al.
6,589,172 B2 7/2003 Williams et al.
6,591,122 B2 7/2003 Schmitt
6,591,123 B2 7/2003 Fein et al.
6,594,511 B2 7/2003 Stone et al.
6,594,512 B2 7/2003 Huang
6,594,513 B1 7/2003 Jobsis et al.
6,597,931 B1 7/2003 Cheng et al.
6,597,933 B2 7/2003 Kiani et al.
6,600,940 B1 7/2003 Fein et al.
6,606,509 B2 8/2003 Schmitt
6,606,510 B2 8/2003 Swedlow et al.
6,606,511 B1 8/2003 Ali et al.
6,606,512 B2 8/2003 Muz et al.
6,615,064 B1 9/2003 Aldrich
6,615,065 B1 9/2003 Barrett et al.
6,618,602 B2 9/2003 Levin et al.
6,622,034 B1 9/2003 Gorski et al.
6,622,095 B2 9/2003 Kobayashi et al.
6,628,975 B1 9/2003 Fein et al.
6,631,281 B1 10/2003 Kästle
6,643,530 B2 11/2003 Diab et al.
6,643,531 B1 11/2003 Katarow
6,647,279 B2 11/2003 Pologe
6,647,280 B2 11/2003 Bahr et al.
6,650,917 B2 * 11/2003 Diab et al. .................... 600/323
6,650,918 B2 11/2003 Terry
6,654,621 B2 11/2003 Palatnik et al.
6,654,622 B1 11/2003 Eberhard et al.
6,654,623 B1 11/2003 Kästle
6,654,624 B2 11/2003 Diab et al.
6,658,276 B2 12/2003 Kianl et al.
6,658,277 B2 12/2003 Wasserman
6,662,030 B2 12/2003 Khalil et al.
6,662,033 B2 12/2003 Casciani et al.
6,665,551 B1 12/2003 Suzuki
6,668,182 B2 12/2003 Hubelbank
6,668,183 B2 12/2003 Hicks et al.
6,671,526 B1 12/2003 Aoyagi et al.
6,671,528 B2 12/2003 Steuer et al.
6,671,530 B2 12/2003 Chung et al.
6,671,531 B2 12/2003 Al-Ali et al.
6,671,532 B1 12/2003 Fudge et al.
6,675,031 B1 1/2004 Porges et al.
6,678,543 B2 1/2004 Diab et al.
6,681,126 B2 1/2004 Solenberger
6,681,128 B2 1/2004 Steuer et al.
6,681,454 B2 1/2004 Modgil et al.
6,684,090 B2 1/2004 Ali et al.
6,684,091 B2 1/2004 Parker
6,690,958 B1 2/2004 Walker et al.
6,694,160 B2 2/2004 Chin
6,697,653 B2 2/2004 Hanna
6,697,655 B2 2/2004 Sueppel et al.
6,697,656 B1 2/2004 Al-Ali
6,697,658 B2 2/2004 Al-Ali
RE38,476 E 3/2004 Diab et al.
6,699,194 B1 3/2004 Diab et al.
6,699,199 B2 3/2004 Asada et al.
6,701,170 B2 3/2004 Stetson
6,702,752 B2 3/2004 Dekker
6,707,257 B2 3/2004 Norris
6,708,048 B1 3/2004 Chance
6,708,049 B1 3/2004 Berson et al.
6,709,402 B2 3/2004 Dekker
6,711,424 B1 3/2004 Fine et al.
6,711,425 B1 3/2004 Reuss
6,714,803 B1 3/2004 Mortz
6,714,804 B2 3/2004 Al-Ali et al.
6,714,805 B2 3/2004 Jeon et al.
RE38,492 E 4/2004 Diab et al.
6,719,686 B2 4/2004 Coakley et al.
6,719,705 B2 4/2004 Mills
6,720,734 B2 4/2004 Norris
6,721,584 B2 4/2004 Baker, Jr. et al.
6,721,585 B1 4/2004 Parker
6,725,074 B1 4/2004 Kästle
6,725,075 B2 4/2004 Al-Ali
6,731,963 B2 5/2004 Finarov et al.
6,731,967 B1 5/2004 Turcott
6,735,459 B2 5/2004 Parker
6,745,060 B2 6/2004 Diab et al.
6,745,061 B1 6/2004 Hicks et al.
6,748,253 B2 6/2004 Norris et al.
6,748,254 B2 6/2004 O'Neil et al.
6,754,515 B1 6/2004 Pologe
6,754,516 B2 6/2004 Mannheimer
6,760,607 B2 7/2004 Al-All
6,760,609 B2 7/2004 Jacques
6,760,610 B2 7/2004 Tschupp et al.
6,763,255 B2 7/2004 DeLonzor et al.
6,763,256 B2 7/2004 Kimball et al.
6,770,028 B1 * 8/2004 Ali et al. ....................... 600/300
6,771,994 B2 8/2004 Kiani et al.
6,773,397 B2 8/2004 Kelly
6,778,923 B2 8/2004 Norris et al.
6,780,158 B2 8/2004 Yarita
6,785,568 B2 8/2004 Chance
6,792,300 B1 9/2004 Diab et al.
6,793,654 B2 9/2004 Lemberg
6,801,797 B2 10/2004 Mannheimer et al.
6,801,798 B2 10/2004 Geddes et al.
6,801,799 B2 10/2004 Mendelson
6,801,802 B2 10/2004 Sitzman et al.

| | | | |
|---|---|---|---|
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,813,511 | B2 | 11/2004 | Diab et al. |
| 6,816,741 | B2 | 11/2004 | Diab |
| 6,819,950 | B2 | 11/2004 | Mills |
| 6,822,564 | B2 | 11/2004 | Al-Ali |
| 6,825,619 | B2 | 11/2004 | Norris |
| 6,826,419 | B2 | 11/2004 | Diab et al. |
| 6,829,496 | B2 | 12/2004 | Nagai et al. |
| 6,830,711 | B2 | 12/2004 | Mills et al. |
| 6,836,679 | B2 | 12/2004 | Baker, Jr. et al. |
| 6,839,579 | B1 | 1/2005 | Chin |
| 6,839,580 | B2 | 1/2005 | Zonios et al. |
| 6,839,582 | B2 | 1/2005 | Heckel |
| 6,839,659 | B2 | 1/2005 | Tarassenko et al. |
| 6,842,635 | B1 | 1/2005 | Parker |
| 6,845,256 | B2 | 1/2005 | Chin et al. |
| 6,850,787 | B2 | 2/2005 | Weber et al. |
| 6,850,788 | B2 | 2/2005 | Al-Ali |
| 6,850,789 | B2 | 2/2005 | Schweitzer, Jr. et al. |
| 6,861,639 | B2 | 3/2005 | Al-Ali |
| 6,863,652 | B2 | 3/2005 | Huang et al. |
| 6,865,407 | B2 | 3/2005 | Kimball et al. |
| 6,873,865 | B2 | 3/2005 | Steuer et al. |
| 6,879,850 | B2 | 4/2005 | Kimball |
| 6,882,874 | B2 | 4/2005 | Huiku |
| 6,889,153 | B2 | 5/2005 | Dietiker |
| 6,898,452 | B2 | 5/2005 | Al-Ali et al. |
| 6,909,912 | B2 | 6/2005 | Melker et al. |
| 6,912,413 | B2 | 6/2005 | Rantala et al. |
| 6,916,289 | B2 | 7/2005 | Schnall |
| 6,920,345 | B2 | 7/2005 | Al-Ali et al. |
| 6,931,269 | B2 | 8/2005 | Terry |
| 6,934,570 | B2 | 8/2005 | Kiani et al. |
| 6,939,307 | B1 | 9/2005 | Dunlop |
| 6,941,162 | B2 | 9/2005 | Fudge et al. |
| 6,947,781 | B2 | 9/2005 | Asada et al. |
| 6,949,081 | B1 | 9/2005 | Chance |
| 6,950,687 | B2 | 9/2005 | Al-Ali |
| 6,961,598 | B2 | 11/2005 | Diab |
| 6,963,767 | B2 | 11/2005 | Rantala et al. |
| 6,971,580 | B2 | 12/2005 | Zhu et al. |
| 6,982,928 | B2 | 1/2006 | Al-Ali |
| 6,983,178 | B2 | 1/2006 | Fine et al. |
| 6,985,763 | B2 | 1/2006 | Boas et al. |
| 6,985,764 | B2 | 1/2006 | Mason et al. |
| 6,990,426 | B2 | 1/2006 | Yoon et al. |
| 6,992,772 | B2 | 1/2006 | Block et al. |
| 6,993,371 | B2 | 1/2006 | Kiani et al. |
| 6,993,372 | B2 | 1/2006 | Fine et al. |
| 6,996,427 | B2 | 2/2006 | Ali et al. |
| 7,003,338 | B2 | 2/2006 | Weber et al. |
| 7,003,339 | B2 | 2/2006 | Diab et al. |
| 7,006,855 | B1 | 2/2006 | Sarussi |
| 7,006,856 | B2 | 2/2006 | Baker, Jr. et al. |
| 7,016,715 | B2 | 3/2006 | Stetson |
| 7,020,507 | B2 | 3/2006 | Scharf et al. |
| 7,024,233 | B2 | 4/2006 | Ali et al. |
| 7,024,235 | B2 | 4/2006 | Melker et al. |
| 7,025,728 | B2 | 4/2006 | Ito et al. |
| 7,027,849 | B2 | 4/2006 | Al-Ali et al. |
| 7,027,850 | B2 | 4/2006 | Wasserman |
| 7,035,697 | B1 | 4/2006 | Brown |
| 7,039,449 | B2 | 5/2006 | Al-Ali |
| 7,043,289 | B2 | 5/2006 | Fine et al. |
| 7,047,055 | B2 | 5/2006 | Boaz et al. |
| 7,047,056 | B2 | 5/2006 | Hannula et al. |
| 7,060,035 | B2 | 6/2006 | Wasserman et al. |
| 7,062,307 | B2 | 6/2006 | Norris et al. |
| 7,067,893 | B2 | 6/2006 | Mills et al. |
| 7,072,701 | B2 | 7/2006 | Chen et al. |
| 7,072,702 | B2 | 7/2006 | Edgar, Jr. et al. |
| 7,079,880 | B2 | 7/2006 | Stetson |
| 7,085,597 | B2 | 8/2006 | Fein et al. |
| 7,096,054 | B2 | 8/2006 | Abdul-Hafiz et al. |
| 7,107,088 | B2 | 9/2006 | Aceti |
| 7,113,815 | B2 | 9/2006 | O'Neil et al. |
| 7,123,950 | B2 | 10/2006 | Mannheimer |
| 7,127,278 | B2 | 10/2006 | Melker et al. |
| 7,130,671 | B2 | 10/2006 | Baker, Jr. et al. |
| 7,132,641 | B2 | 11/2006 | Schulz et al. |
| 7,133,711 | B2 | 11/2006 | Chernoguz et al. |
| 7,139,599 | B2 | 11/2006 | Terry |
| 7,142,901 | B2 | 11/2006 | Kiani et al. |
| 7,162,288 | B2 | 1/2007 | Nordstrom |
| 7,190,987 | B2 | 3/2007 | Lindekugel et al. |
| 7,198,778 | B2 | 4/2007 | Achilefu et al. |
| 7,209,775 | B2 | 4/2007 | Bae et al. |
| 7,215,984 | B2 | 5/2007 | Diab et al. |
| 7,225,006 | B2 | 5/2007 | Al-Ali et al. |
| 7,236,811 | B2 | 6/2007 | Schmitt |
| 7,248,910 | B2 | 7/2007 | Li et al. |
| 7,254,433 | B2 | 8/2007 | Diab et al. |
| 7,254,434 | B2 | 8/2007 | Schulz et al. |
| 7,263,395 | B2 | 8/2007 | Chan et al. |
| 7,272,426 | B2 | 9/2007 | Scmid |
| 7,280,858 | B2 | 10/2007 | Al-Ali et al. |
| 7,295,866 | B2 | 11/2007 | Al-Ali et al. |
| 7,305,262 | B2 | 12/2007 | Brodnick et al. |
| 7,315,753 | B2 | 1/2008 | Baker, Jr. et al. |
| 2001/0005773 | A1 | 6/2001 | Larsen et al. |
| 2001/0020122 | A1 | 9/2001 | Steuer et al. |
| 2001/0021803 | A1 | 9/2001 | Blank et al. |
| 2001/0039376 | A1 | 11/2001 | Steuer et al. |
| 2001/0044700 | A1 | 11/2001 | Kobayashi et al. |
| 2001/0051767 | A1 | 12/2001 | Williams et al. |
| 2002/0026106 | A1 | 2/2002 | Khalil et al. |
| 2002/0026109 | A1 | 2/2002 | Diab et al. |
| 2002/0028990 | A1 | 3/2002 | Sheperd et al. |
| 2002/0035318 | A1 | 3/2002 | Mannheimer et al. |
| 2002/0038078 | A1 | 3/2002 | Ito |
| 2002/0038079 | A1 | 3/2002 | Steuer et al. |
| 2002/0042558 | A1 | 4/2002 | Mendelson |
| 2002/0049389 | A1 | 4/2002 | Abreu |
| 2002/0062071 | A1 | 5/2002 | Diab et al. |
| 2002/0068859 | A1 | 6/2002 | Knopp |
| 2002/0111748 | A1 | 8/2002 | Kobayashi et al. |
| 2002/0123672 | A1* | 9/2002 | Christophersom et al. ... 600/300 |
| 2002/0128544 | A1 | 9/2002 | Diab et al. |
| 2002/0133067 | A1 | 9/2002 | Jackson, III |
| 2002/0133068 | A1 | 9/2002 | Huiku |
| 2002/0156354 | A1 | 10/2002 | Larson |
| 2002/0161287 | A1 | 10/2002 | Schmitt |
| 2002/0161290 | A1 | 10/2002 | Chance |
| 2002/0165439 | A1* | 11/2002 | Schmitt ........................ 600/309 |
| 2002/0173706 | A1 | 11/2002 | Takatani |
| 2002/0173709 | A1 | 11/2002 | Fine et al. |
| 2002/0190863 | A1 | 12/2002 | Lynn |
| 2002/0198442 | A1 | 12/2002 | Rantala et al. |
| 2002/0198443 | A1 | 12/2002 | Ting |
| 2003/0018243 | A1 | 1/2003 | Gerhardt et al. |
| 2003/0023140 | A1 | 1/2003 | Chance |
| 2003/0036690 | A1 | 2/2003 | Geddes et al. |
| 2003/0045785 | A1 | 3/2003 | Diab et al. |
| 2003/0055324 | A1 | 3/2003 | Wasserman |
| 2003/0060693 | A1 | 3/2003 | Monfre et al. |
| 2003/0073889 | A1 | 4/2003 | Keilbach et al. |
| 2003/0073890 | A1 | 4/2003 | Hanna |
| 2003/0100840 | A1 | 5/2003 | Sugiura et al. |
| 2003/0132495 | A1 | 7/2003 | Mills et al. |
| 2003/0135099 | A1 | 7/2003 | Al-Ali |
| 2003/0139687 | A1 | 7/2003 | Abreu |
| 2003/0144584 | A1 | 7/2003 | Mendelson |
| 2003/0162414 | A1 | 8/2003 | Schulz et al. |
| 2003/0171662 | A1 | 9/2003 | O'Connor et al. |
| 2003/0176776 | A1 | 9/2003 | Huiku |
| 2003/0181799 | A1 | 9/2003 | Lindekugel et al. |
| 2003/0187337 | A1 | 10/2003 | Tarassenko et al. |
| 2003/0195402 | A1 | 10/2003 | Fein et al. |
| 2003/0197679 | A1 | 10/2003 | Ali et al. |
| 2003/0212316 | A1 | 11/2003 | Leiden et al. |
| 2003/0220548 | A1 | 11/2003 | Schmitt |
| 2003/0220576 | A1 | 11/2003 | Diab |
| 2003/0225323 | A1 | 12/2003 | Kiani et al. |
| 2003/0225337 | A1 | 12/2003 | Scharf et al. |
| 2003/0236452 | A1 | 12/2003 | Melker et al. |
| 2003/0236647 | A1 | 12/2003 | Yoon et al. |

| | | | |
|---|---|---|---|
| 2004/0006261 | A1 | 1/2004 | Swedlow et al. |
| 2004/0010188 | A1 | 1/2004 | Wasserman et al. |
| 2004/0024297 | A1 | 2/2004 | Chen et al. |
| 2004/0024326 | A1 | 2/2004 | Yeo et al. |
| 2004/0034293 | A1 | 2/2004 | Kimball |
| 2004/0039272 | A1 | 2/2004 | Abdul-Hafiz et al. |
| 2004/0039273 | A1 | 2/2004 | Terry |
| 2004/0054269 | A1 | 3/2004 | Rantala et al. |
| 2004/0054270 | A1 | 3/2004 | Pewzner et al. |
| 2004/0054291 | A1 | 3/2004 | Schulz et al. |
| 2004/0059209 | A1 | 3/2004 | Al-Ali et al. |
| 2004/0059210 | A1 | 3/2004 | Stetson |
| 2004/0064020 | A1 | 4/2004 | Diab et al. |
| 2004/0068164 | A1 | 4/2004 | Diab et al. |
| 2004/0087846 | A1 | 5/2004 | Wasserman |
| 2004/0092805 | A1 | 5/2004 | Yarita |
| 2004/0097797 | A1 | 5/2004 | Porges et al. |
| 2004/0098009 | A1 | 5/2004 | Boecker et al. |
| 2004/0107065 | A1 | 6/2004 | Al-Ali et al. |
| 2004/0116788 | A1 | 6/2004 | Chernoguz et al. |
| 2004/0116789 | A1 | 6/2004 | Boaz et al. |
| 2004/0117891 | A1 | 6/2004 | Hannula et al. |
| 2004/0122300 | A1 | 6/2004 | Boas et al. |
| 2004/0122302 | A1 | 6/2004 | Mason et al. |
| 2004/0127779 | A1 | 7/2004 | Steuer et al. |
| 2004/0133087 | A1 | 7/2004 | Ali et al. |
| 2004/0133088 | A1 | 7/2004 | Al-Ali et al. |
| 2004/0138538 | A1 | 7/2004 | Stetson |
| 2004/0138540 | A1 | 7/2004 | Baker, Jr. et al. |
| 2004/0143172 | A1 | 7/2004 | Fudge et al. |
| 2004/0147821 | A1 | 7/2004 | Al-Ali et al. |
| 2004/0147822 | A1 | 7/2004 | Al-Ali et al. |
| 2004/0147823 | A1 | 7/2004 | Kiani et al. |
| 2004/0147824 | A1 | 7/2004 | Diab et al. |
| 2004/0152965 | A1 | 8/2004 | Diab et al. |
| 2004/0158134 | A1 | 8/2004 | Diab et al. |
| 2004/0158135 | A1 | 8/2004 | Baker, Jr. et al. |
| 2004/0162472 | A1 | 8/2004 | Berson et al. |
| 2004/0171920 | A1 | 9/2004 | Mannheimer et al. |
| 2004/0171948 | A1 | 9/2004 | Terry |
| 2004/0176670 | A1 | 9/2004 | Takamura et al. |
| 2004/0176671 | A1 | 9/2004 | Fine et al. |
| 2004/0181133 | A1 | 9/2004 | Al-Ali et al. |
| 2004/0181134 | A1 | 9/2004 | Baker, Jr. et al. |
| 2004/0186358 | A1 | 9/2004 | Chernow et al. |
| 2004/0199063 | A1 | 10/2004 | O'Neil et al. |
| 2004/0204636 | A1 | 10/2004 | Diab et al. |
| 2004/0204637 | A1 | 10/2004 | Diab et al. |
| 2004/0204638 | A1 | 10/2004 | Diab et al. |
| 2004/0204639 | A1 | 10/2004 | Casciani et al. |
| 2004/0204865 | A1 | 10/2004 | Lee et al. |
| 2004/0210146 | A1 | 10/2004 | Diab et al. |
| 2004/0215069 | A1 | 10/2004 | Mannheimer |
| 2004/0230106 | A1 | 11/2004 | Schmitt et al. |
| 2004/0230107 | A1 | 11/2004 | Asada et al. |
| 2004/0230108 | A1 | 11/2004 | Melker et al. |
| 2004/0236196 | A1 | 11/2004 | Diab et al. |
| 2004/0242980 | A1 | 12/2004 | Kiani et al. |
| 2004/0249252 | A1 | 12/2004 | Fine et al. |
| 2004/0257557 | A1 | 12/2004 | Block et al. |
| 2004/0260161 | A1 | 12/2004 | Melker et al. |
| 2004/0260186 | A1 | 12/2004 | Dekker |
| 2004/0267103 | A1 | 12/2004 | Li et al. |
| 2004/0267104 | A1 | 12/2004 | Hannula et al. |
| 2004/0267140 | A1 | 12/2004 | Ito et al. |
| 2005/0004479 | A1 | 1/2005 | Townsend et al. |
| 2005/0010092 | A1 | 1/2005 | Weber et al. |
| 2005/0020887 | A1 | 1/2005 | Goldberg |
| 2005/0020894 | A1 | 1/2005 | Norris et al. |
| 2005/0033128 | A1 | 2/2005 | Ali et al. |
| 2005/0033129 | A1 | 2/2005 | Edgar, Jr. et al. |
| 2005/0043599 | A1 | 2/2005 | O'Mara |
| 2005/0043600 | A1 | 2/2005 | Diab et al. |
| 2005/0049470 | A1 | 3/2005 | Terry |
| 2005/0049471 | A1 | 3/2005 | Aceti |
| 2005/0075550 | A1 | 4/2005 | Lindekugel |
| 2005/0080323 | A1 | 4/2005 | Kato |
| 2005/0101850 | A1 | 5/2005 | Parker |
| 2005/0113656 | A1 | 5/2005 | Chance |
| 2005/0168722 | A1 | 8/2005 | Forstner et al. |
| 2005/0177034 | A1 | 8/2005 | Beaumont |
| 2005/0192488 | A1 | 9/2005 | Bryenton et al. |
| 2005/0197548 | A1 | 9/2005 | Dietiker |
| 2005/0203357 | A1 | 9/2005 | Debreczeny et al. |
| 2005/0228248 | A1 | 10/2005 | Dietiker |
| 2005/0267346 | A1 | 12/2005 | Faber et al. |
| 2005/0277819 | A1 | 12/2005 | Kiani et al. |
| 2005/0283059 | A1 | 12/2005 | Iyer et al. |
| 2005/0284476 | A1* | 12/2005 | Blanch et al. ............ 128/204.21 |
| 2006/0009688 | A1 | 1/2006 | Lamego et al. |
| 2006/0015021 | A1 | 1/2006 | Cheng |
| 2006/0020181 | A1 | 1/2006 | Schmitt |
| 2006/0025660 | A1 | 2/2006 | Swedlow et al. |
| 2006/0030763 | A1 | 2/2006 | Mannheimer et al. |
| 2006/0052680 | A1 | 3/2006 | Diab |
| 2006/0058594 | A1 | 3/2006 | Ishizuka et al. |
| 2006/0058683 | A1 | 3/2006 | Chance |
| 2006/0058691 | A1 | 3/2006 | Kiani |
| 2006/0064024 | A1 | 3/2006 | Schnall |
| 2006/0084852 | A1 | 4/2006 | Mason et al. |
| 2006/0089547 | A1 | 4/2006 | Sarussi |
| 2006/0106294 | A1 | 5/2006 | Maser et al. |
| 2006/0195028 | A1 | 8/2006 | Hannula et al. |
| 2006/0224058 | A1 | 10/2006 | Mannheimer |
| 2006/0247501 | A1 | 11/2006 | Ali |
| 2006/0258921 | A1 | 11/2006 | Addison et al. |
| 2007/0032710 | A1 | 2/2007 | Raridan et al. |
| 2007/0032712 | A1 | 2/2007 | Raridan et al. |
| 2007/0032715 | A1 | 2/2007 | Eghbal et al. |
| 2007/0073126 | A1 | 3/2007 | Raridan, Jr. |
| 2007/0179386 | A1 | 8/2007 | Michard et al. |
| 2008/0200775 | A1 | 8/2008 | Lynn |
| 2009/0076462 | A1 | 3/2009 | Kiani |

FOREIGN PATENT DOCUMENTS

| | | | |
|---|---|---|---|
| EP | 0630203 | | 12/1994 |
| JP | 63275325 | | 11/1988 |
| JP | 2005034472 | | 2/2005 |
| WO | WO9639927 | | 12/1996 |
| WO | WO0021438 | | 4/2000 |
| WO | WO0140776 | | 6/2001 |
| WO | WO0176461 | | 10/2001 |
| WO | WO0176471 | | 10/2001 |
| WO | 02/075289 | A2 | 9/2002 |
| WO | WO03039326 | | 5/2003 |
| WO | 2006086085 | A2 | 8/2006 |
| WO | 2008073855 | A2 | 6/2008 |

OTHER PUBLICATIONS

Variations in arterial blood pressure and photoplethysmography during mechanical ventilation. Natalini G, Rosano A, Franceschetti ME, Facchetti P, Bernardini A. Anesth Analg. Nov. 2006;103(5):1182-8.*

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

East, Christine E., et al.; "Fetal Oxygen Saturation and Uterine Contractions During Labor," *American Journal of Perinatology*, vol. 15, No. 6, pp. 345-349 (Jun. 1998).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).
A. Johansson; "Neural network for photoplethysmographic respiratory rate monitoring," *Medical & Biological Engineering & Computing*, vol. 41, pp. 242-248 (2003).
Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.
Spigulis, Janis, et al.; "Optical multi-channel sensing of skin blood pulsations," *Optical Sensing, Proceedings of SPIE*, vol. 5459, pp. 46-53 (2004).
PCT Notification of Transmittal of the International Search Report and the Written Opinion of the the International Searching Authority, or the Declaration, Date of mailing: Jun. 17, 2010, Applicants file reference: H-RM-01331 WO, International application No. PCT/US2010/027508, International filing date: Mar. 16, 2010, Applicant: Nellcor Puritan Bennett LLC.

* cited by examiner

MEDICAL DEVICE FOR ASSESSING INTRAVASCULAR BLOOD VOLUME AND TECHNIQUE FOR USING THE SAME

BACKGROUND

The present disclosure relates generally to a method and system for monitoring physiological parameters of a patient. Specifically, embodiments of the present invention relate to more accurate estimation of intravascular blood volume and fluid responsiveness by adjusting pulse oximetry waveform measurements to account for variations in respiratory parameters and/or other patient parameters.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One physiological parameter that physicians may wish to monitor is blood fluid volume (i.e., intravascular volume). Variations from normal fluid volume in the blood may indicate a change in clinical condition or an injury. For example, hypovolemia is a state of decreased intravascular volume that may be associated with dehydration. Correct clinical assessment of hypovolemia is complex. More specifically, intravascular volume is difficult to estimate, particularly in critically ill patients. Without an accurate assessment of a patient's intravascular volume, it is difficult to predict whether a patient will respond to fluid therapy (e.g., a blood or fluid infusion) with an improvement in clinical condition, such as an increase in stroke volume and cardiac output. Accordingly, accurate assessments of intravascular volume may assist a clinician in determining whether a patient will be responsive to fluid therapy.

To this end, indicators such as the systolic blood pressure variation, pulse pressure variation, or stroke volume variation may be used to estimate intravascular volume and determine whether a patient is likely to be fluid responsive. However, these measurements tend to be invasive. For example, to obtain an accurate pulse pressure waveform from which the intravascular volume can be determined, a physician may insert an invasive arterial line.

BRIEF DESCRIPTION OF THE DRAWINGS

Advantages of the disclosure may become apparent upon reading the following detailed description and upon reference to the drawings in which.

DETAILED DESCRIPTION

Figure 1:
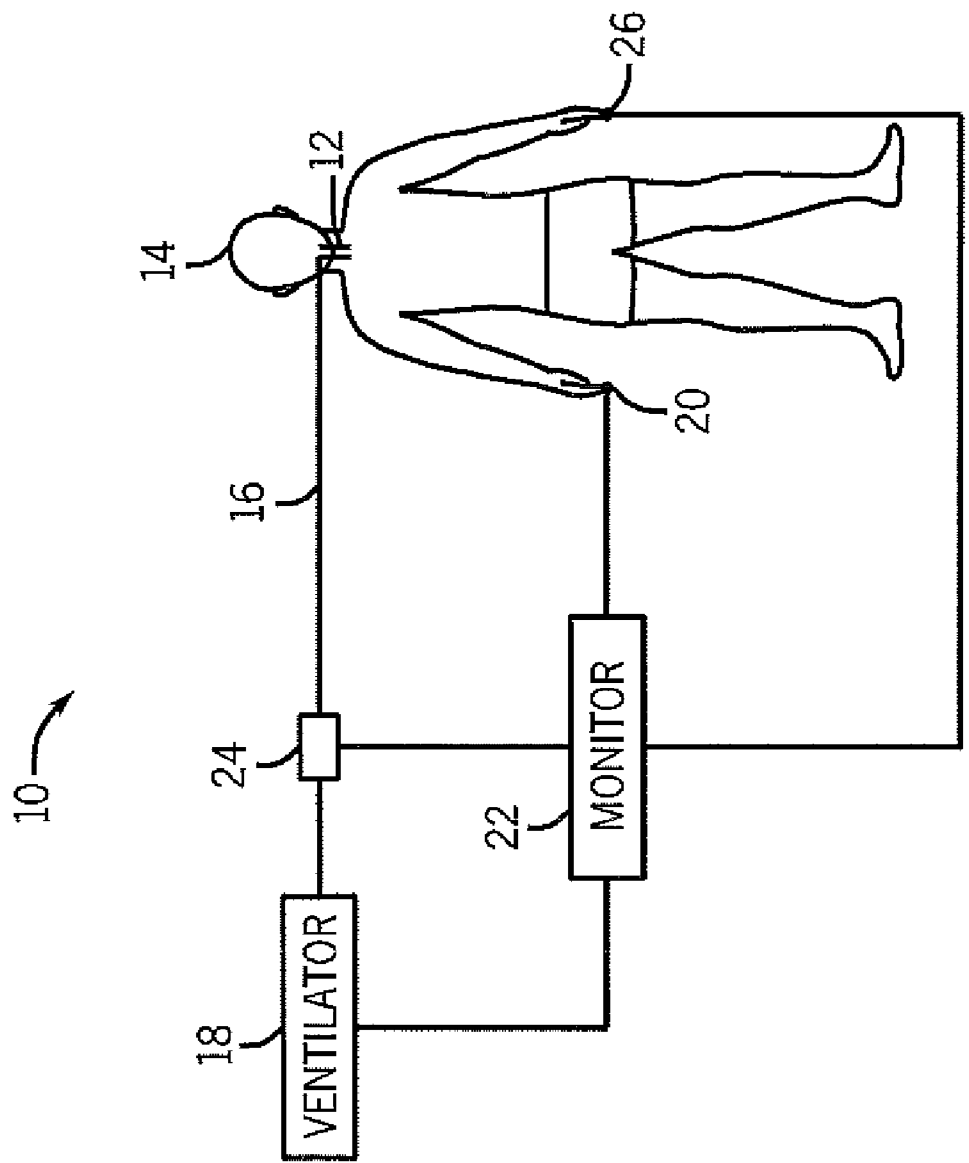
FIG. 1 is a block diagram of a ventilation system for determining intravascular blood volume in accordance with an embodiment.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

For patients who are undergoing multiple and overlapping medical treatments, monitoring physiological parameters may be complex. For example, certain physiological characteristics of the patient may be influenced by the medical treatment being provided. In embodiments, a ventilator may control a patient's breathing rate along with the type and amount of gases inhaled. Because respiration affects the delivery of oxygen from the lungs into the blood, changes in ventilation parameters and/or patient lung conditions may result in changes to hemodynamic parameters, such as pulse pressure and blood oxygenation.

The variability in a waveform representative of a patient's blood oxygen levels (i.e., a plethysmographic waveform) may be used to estimate a patient's intravascular volume. Blood oxygen levels may be monitored with a on-invasive, optical pulse oximetry sensor that transmits two or more wavelengths of light, most commonly red and near infrared wavelengths, through a patient's tissue and that photoelectrically detects the absorption and/or scattering of the transmitted light in such tissue. The use of pulse oximetry to estimate intravascular volume and fluid responsiveness in ventilated patients provides the ease of use of a noninvasive, rather than invasive, sensor. However, as noted, blood oxygen measurements may be affected by other clinical conditions, such as respiratory parameters. For example, the plethysmographic waveform signal may be sensitive to respiratory parameters, such as respiration rate, tidal volume, end tidal carbon dioxide concentration, or positive end-expiratory pressure, which may be controlled by particular settings on a ventilator. In addition, the plethysmographic waveform signal may be sensitive to tissue or blood constituent concentration, for example, a tissue water fraction or a partial pressure of carbon dioxide in the tissue. Further, the plethysmographic waveform signal may have certain patient-to-patient variability based on age, weight, gender, and clinical condition.

The plethysmographic waveform signal, or, in embodiments, a calculated value based on variation in the waveform signal, may be corrected or adjusted to provide a more accurate estimate of intravascular volume. A clinician may use the estimate of intravascular volume to make determinations about a patient's clinical condition, such as the likelihood that the patient will respond to fluid therapy. The adjustment may correct for certain physiological conditions that may influence the plethysmographic waveform and that may either mask or exaggerate the plethysmographic waveform variability. For example, in the case of a ventilated patient with a controlled respiration rate, the patient's blood oxygen saturation may be higher relative to a patient who is not receiving breathing assistance. Depending on the patient's clinical condition, a ventilated patient with generally higher respiration rate may have greater peak-to-peak variability in a plethysmographic waveform, which in turn would result in a higher calculated variability value. Typically, higher variability values (e.g., greater than 15% variability) may be associated with increased fluid responsiveness. Accordingly, an artificially high variability value may mask a patient's true fluid responsiveness.

By correcting the variability of the plethysmographic signal to account for the influence of patient parameters, such as a higher respiration rate as a result of ventilation, the resulting plethysmographic waveform variability value may be more accurate. Accordingly, a clinician may be able to make more informed decisions about whether the patient may benefit from fluid therapy. In addition, the clinician may be able to assess changes in blood volume more rapidly and may be able to intervene to provide therapy to the patient at an earlier time point. In embodiments, a closed-loop system is provided in which the corrected plethysmographic waveform variability is used to estimate the intravascular volume and determine the fluid responsiveness of a patient. A closed-loop controller may control delivery of fluid therapy if the estimate of intravascular volume is associated with hypovolemia, which may indicate that the patient will be responsive to fluid therapy.

Embodiments provided herein are directed to medical devices for assessing intravascular volume based on respiratory or other patient parameters. Suitable devices may be incorporated into a respiratory system 10, shown in FIG. 1, or any other patient monitoring system. In one embodiment, the respiratory system 10 may include a tracheal tube 12, such as an endotracheal tube, that is inserted into a patient 14 to deliver gases to and from the patient's lungs. The respiratory system 10 may also include a respiratory circuit 16 connecting the tracheal tube 12 to a ventilator 18. In embodiments, the ventilator 18 may be a positive pressure ventilator, such as those available from Nellcor Puritan Bennett LLC.

The system 10 may also include a pulse oximetry sensor 20 for generating a plethysmographic waveform signal representative of a patient's blood oxygen levels. The pulse oximetry sensor 20 may be in communication with a monitor 22 configured to receive the plethysmographic waveform signal and estimate the patient's intravascular volume and/or fluid responsiveness. In one embodiment, the monitoring functions of the monitor 22 may be incorporated into a single device that also performs the functions of ventilator 18.

In embodiments, the plethysmographic waveform variability may be corrected by adjusting for respiratory parameters controlled by the ventilator 18. For example, the ventilator 18 may include a controller for controlling respiration rate, tidal volume, flow rate, pressure, peak airway pressure, ratio of expiration to inspiration time, fraction of inspired oxygen (i.e., the percentage of oxygen in the gas mixture), inspired pressure increases or decreases over each breath (e.g., positive end-expiratory pressure), and any other respiratory parameter. Any suitable respiratory parameter controlled by the ventilator 18 may be used to adjust an estimate of intravascular volume, as discussed in more detail below.

The respiratory system 10 may also include any number or combination of additional sensors for providing information related to patient parameters that may be used to correct or adjust the estimate of the patient's intravascular volume and/or fluid responsiveness. For example, suitable sensors may include sensors for determining tissue hydration, tissue constituents, blood constituents, blood pressure, heart rate, patient temperature, or tissue impedance. Such sensors may also include sensors for determining the presence or concentration of biomarkers, including sensors for circulating biomarkers related to cardiac stress and function (e.g., troponin or cholesterol) and/or biomarkers associated with lung function (e.g., surfactant protein D).

Suitable sensors for providing information about additional patient parameters may be optical, electrical, chemical, or biological sensors. A carbon dioxide sensor or tissue water fraction sensor may direct two or more wavelengths of light, most commonly near infrared wavelengths between about 1,000 nm to about 2,500 nm, into a sample, e.g., a gas sample or a tissue sample. Other sensors may include electrical sensors, such as electrical impedance sensors that may sense a voltage drop between two electrodes that are applied to a patient's tissue. Chemical sensors may include calorimetric chemical sensors, such as calorimetric sensors for detection of carbon dioxide. For example, a chemical sensor for carbon dioxide may include an indicator solution containing hydroxyl ions or amine residues that react chemically with carbon dioxide to form a carbonate and/or a bicarbonate or carbamate moiety, such as those discussed in co-pending U.S. Patent Publication No. 2008/0078394 by Ostrowski et al., filed on Sep. 25, 2006, the specification of which is incorporated by reference in its entirety herein for all purposes. This reaction may ultimately result in a color change that may be optically detected. Biological sensors may include enzymatic sensors for detecting a color or fluorescence change produced by enzymatic reactions or by antibody/ligand binding. For example, surfactant protein D may be detected by an enzyme-linked immunosorbent assay available from Cell Sciences (Canton, Mass.).

By way of example, FIG. 1 shows a carbon dioxide sensor 24 that may be associated with the respiratory circuit 16 and an aquametry sensor 26 that may be applied to an appropriate tissue location on the patient 14. However, it should be understood that carbon dioxide sensor 24 and aquametry sensor 26 are merely illustrative of sensor types that may be used in conjunction with the respiratory system 10. The carbon dioxide sensor 24 may be disposed along the respiratory circuit 16 (e.g., within a tube or connector of the respiratory circuit 16) or associated with the respiratory circuit 16. In addition, the carbon dioxide sensor 24 may be applied to a patient's tissue for determining partial pressure of carbon dioxide by optically interrogating the tissue. Carbon dioxide sensor 24 may be connected to downstream monitor 22 and may provide the data used to correct or adjust pulse oximetry variability measurements as provided herein. For example, a carbon dioxide sensor 24 may provide information to the monitor 22 relating to a carbon dioxide concentration in the expired gas stream. Carbon dioxide concentration measurements, e.g., capnography, may be used to estimate carbon dioxide partial pressure in arterial blood. In one embodiment, end-tidal $CO_2$ (the level of carbon dioxide released at the end of expiration) may be determined through capnography, which may be implemented by monitor 22. In other embodiments, the capnography measurements may be performed by a separate processor-based device, or may be performed by the ventilator 18. To coordinate the measurement of end-tidal $CO_2$ with the timing of the expiration, the ventilator 18 may provide information to the monitor 22 relating to the timing of the expiration and inhalation. For example, the respiration timing information may be used to control the carbon dioxide sensor 24.

The respiratory system 10 may include, either instead of or in addition to carbon dioxide sensor/s 24, any number of additional sensor types. For example, aquametry sensor 26 may be a sensor that may be applied to a patient's tissue for determining a tissue water fraction. The aquametry sensor 26 may include any suitable arrangement of optical components for spectrophotometrically assessing the patient's tissue water fraction. In one embodiment, the aquametry sensor 26 and the pulse oximetry sensor 20 may be integrated into a unitary sensor body.

Figure 2:
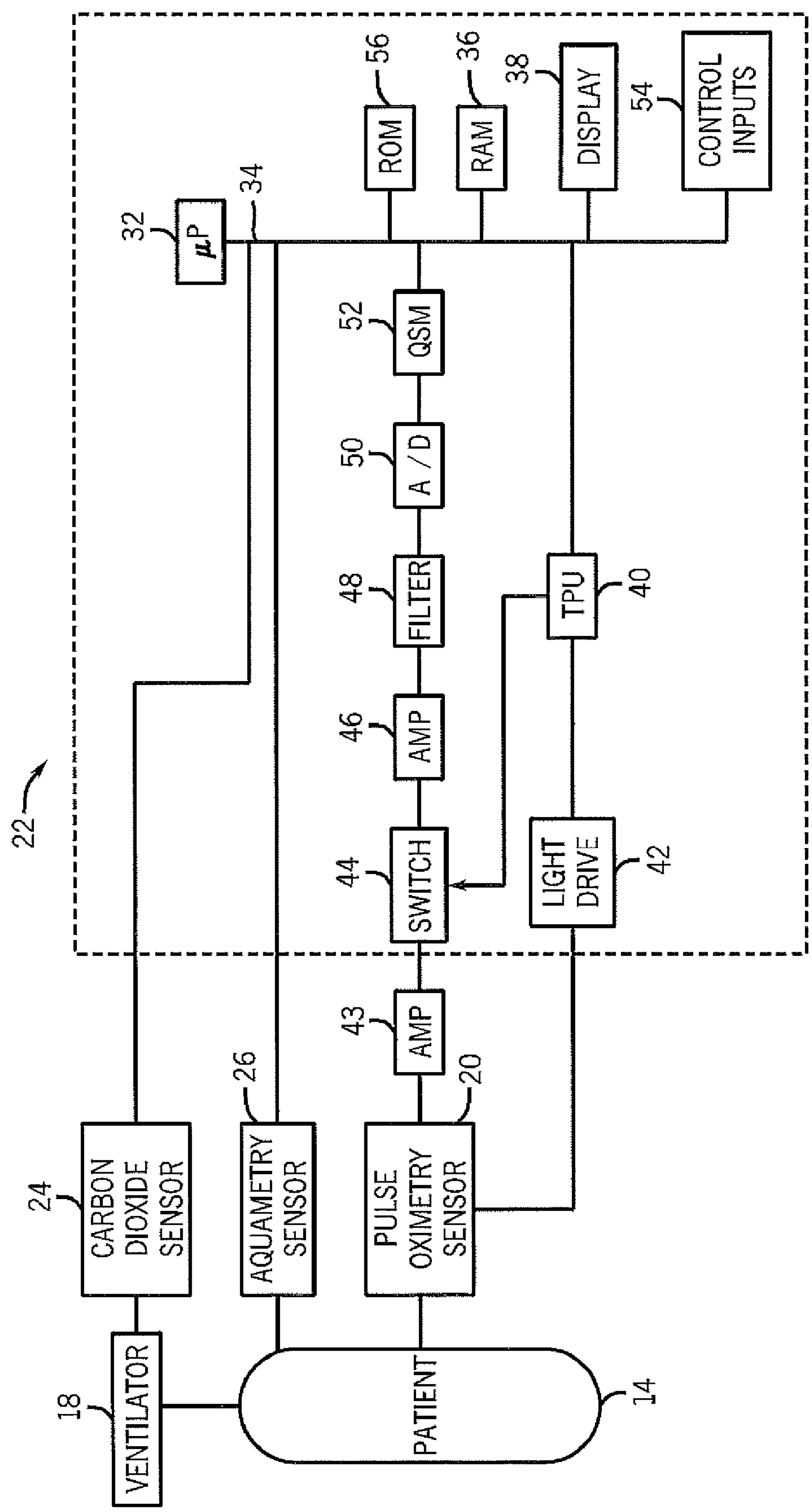
FIG. 2 is a block diagram of a patient monitor that may be used in conjunction with the ventilation system of FIG. 1 in accordance with an embodiment.

The downstream monitor 22 may receive signals, for example from ventilator 18 or from one or more sensors 24 or 26, to correct or adjust pulse oximetry signals received from pulse oximetry sensor 20. FIG. 2 is a block diagram of an embodiment of a monitor 22 that may be configured to implement the embodiments of the present disclosure. The pulse oximetry signal from the pulse oximetry sensor 20 may generate a plethysmographic waveform, which may be further processed and corrected by the monitor 22. The monitor 22 may receive and further process a signal from carbon dioxide sensor 24 to determine a value representative of a concentration of carbon dioxide in the respiratory circuit 16 and/or a signal from aquametry sensor 26 to determine a value representative of a tissue water fraction of the patient.

The monitor 22 may include a microprocessor 32 coupled to an internal bus 34. Also connected to the bus may be a RAM memory 36 and a display 38. A time processing unit (TPU) 40 may provide timing control signals to light drive circuitry 42, which controls when an optical sensor (e.g., pulse oximetry sensor 20, carbon dioxide sensor 24, or tissue water fraction sensor 26) is activated, and, if multiple light sources are used, the multiplexed timing for the different light sources. TPU 40 may also control the gating-in of signals from sensor 20 through an amplifier 43 and a switching circuit 44. These signals are sampled at the proper time, depending at least in part upon which of multiple light sources is activated, if multiple light sources are used. The received signal from the pulse oximetry sensor 20 may be passed through an amplifier 46, a low pass filter 48, and an analog-to-digital converter 50. The digital data may then be stored in a queued serial module (QSM) 52, for later downloading to RAM 36 or ROM 56 as QSM 52 fills up.

In an embodiment, based at least in part upon the received signals corresponding to the light received by optical components of the pulse oximetry sensor 20, microprocessor 32 may calculate the oxygen saturation using various algorithms In addition, the microprocessor 32 may calculate a plethysmographic waveform variation using various algorithms, such as suitable statistical or time-series analysis algorithms. The plethysmograhpic waveform variation may be corrected based on input signals from other sensors (e.g., carbon dioxide sensor 24 or aquametry sensor 26), the ventilator 18, or caregiver inputs to control inputs 54. For example, the caregiver may input a patient's age, weight, gender, or information about the patient's clinical condition that may be relevant to the accurate estimation of the intravascular volume. These algorithms may employ certain coefficients, which may be empirically determined, and may correspond to the wavelengths of light used. In addition, the algorithms may employ additional correction coefficients. By way of example, a particular end tidal carbon dioxide measurement, as generated from a signal provided by carbon dioxide sensor 24, may be associated with a particular correction coefficient. The algorithms and coefficients may be stored in a ROM 56 or other suitable computer-readable storage medium and accessed and operated according to microprocessor 32 instructions. In one embodiment, the correction coefficients may be provided as a lookup table.

Figure 3:
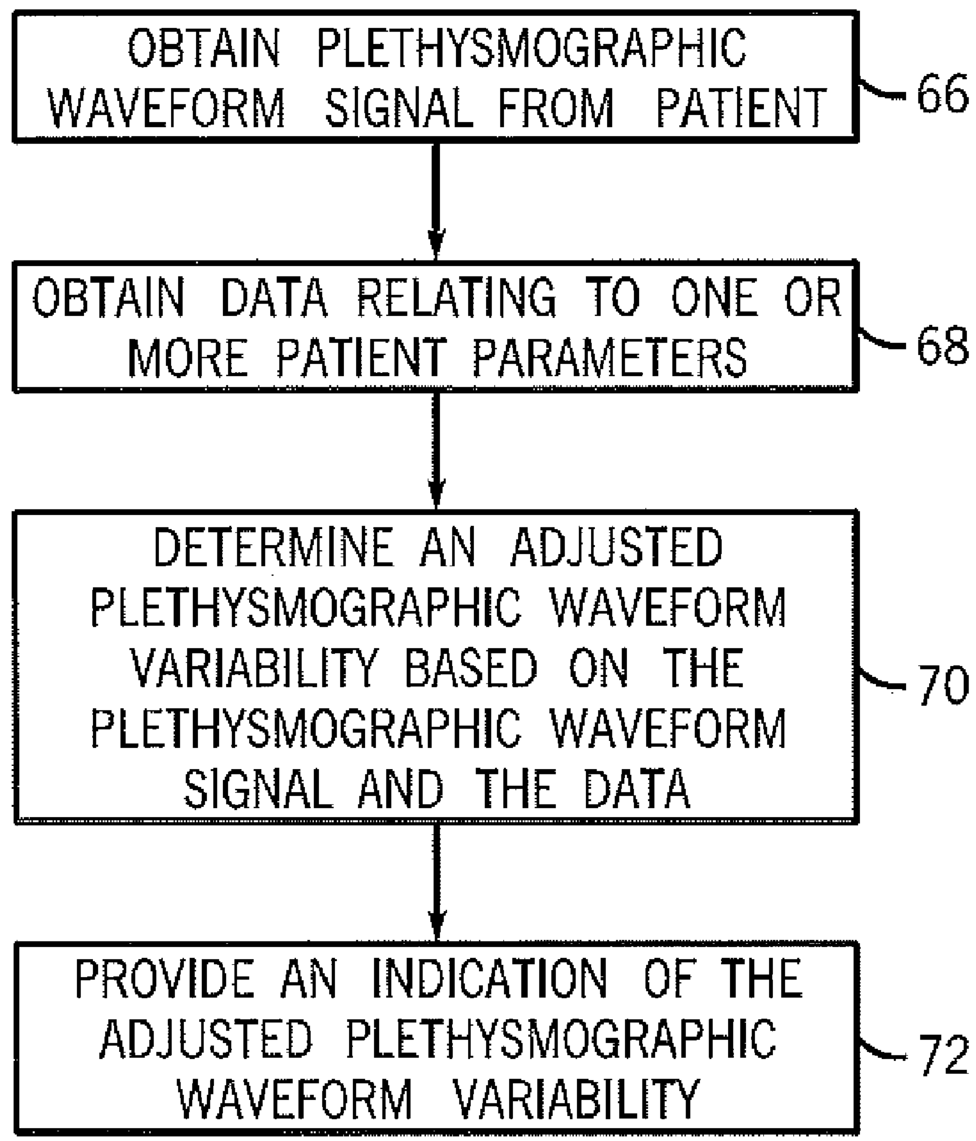
FIG. 3 is a block diagram of a method illustrating an embodiment.

A patient's intravascular volume may be determined based on the corrected variability of a pulse oximetry plethysmographic waveform that is adjusted based on patient parameters. FIG. 3 is a process flow diagram illustrating a method 64 in accordance with some embodiments. The method may be performed as an automated procedure by a system, such as system 10. In addition, certain steps of the method may be performed by a processor, or a processor-based device such as a patient monitor 22 that includes instructions for implementing certain steps of the method 64.

According to an embodiment the method 64 begins with obtaining a plethystnographic waveform signal from a pulse oximetry sensor 20 at step 66. Additional data relating to one or more patient parameters is obtained at step 68. The data relating to one or more patient parameters may be received from the ventilator 18, or may be calculated from signals received from patient sensors, e.g., carbon dioxide sensor 24 or aquametry sensor 26. In addition, the data relating to one or more patient parameters may be manually input by a healthcare provider.

The monitor 22 may perform analysis of the plethysmographic waveform signal and calculation of the plethysmographic waveform variability at step 70 based on the plethysmographic waveform signal obtained at step 66 and the additional patient parameter data obtained at step 68. The mathematical model for adjusting the waveform variability based on additional patient parameters obtained in step 68 may be linear or nonlinear, multivariate, partial least squares, principal component regression, auto-regressive moving average, mathematical curve fitting or simply an additive constant to the variability value. In one embodiment, the waveform variability is first calculated to provide a percentage value, and then the percentage value is adjusted based on the patient parameters.

In embodiments, the plethysmographic waveform signal may be modified or filtered based on the patient parameters prior to the calculation of the waveform variability to provide an adjusted or corrected variability value. For example, if a patient parameter is associated with having a damping effect on the waveform, the damping effect may be quantified and a filter may be used to remove the damping effect. In addition, the variability of the AC component (i.e., the pulsatile component) of the plethysmographic waveform signal, and not the DC component (i.e., the nonpulsatile component), may be used for assessing the intravascular blood volume. Accordingly, the DC component may be filtered out or otherwise removed from the waveform prior to the analysis in step 70.

Figure 4:
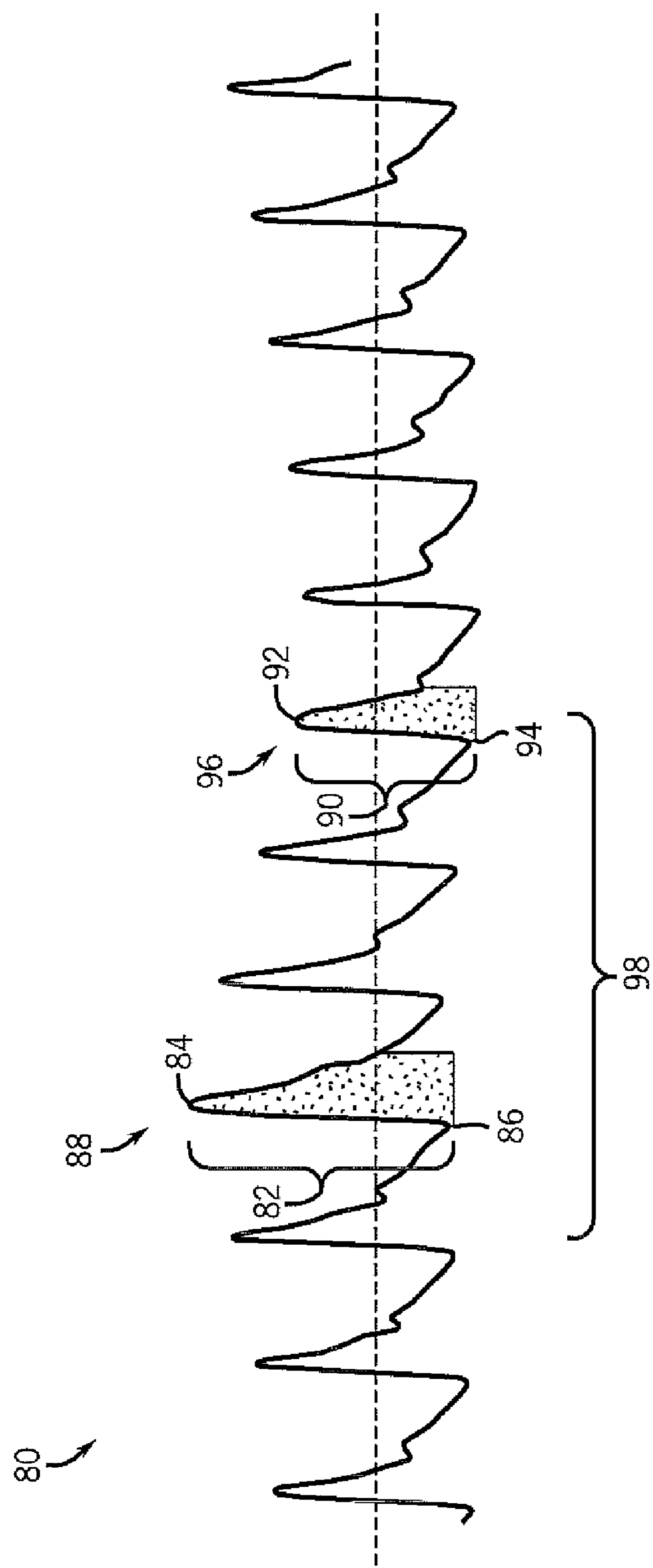
FIG. 4 is a plethysmographic waveform illustrating an embodiment.

FIG. 4 illustrates a plethysmographic waveform 80 from which the plethysmographic waveform variability, $W_v$, may be determined based on the following equation:

$$W_v=(W_{max}-W_{min})/W_{mean}$$

where $W_{max}$ is a maximum peak value, taken as a vertical distance 82 between a peak 84 and trough 86 for a largest peak 88 (i.e., a single cardiac cycle) and $W_{min}$ is a minimum peak value, taken as vertical distance 90 between a peak 92 and trough 94 for a smallest peak 96 within a window 98 of consecutive peaks. $W_{mean}$ represents the mean vertical distance between peak maxima and minima for the consecutive peaks in the window 98. The window 98 may be a total number of peaks, such as 5 consecutive peaks, or may include all consecutive peaks within a time window, such as 10 seconds. In embodiments, an operator may adjust the settings on a monitor to change the size of the window according to the desired monitoring parameters. For example, an operator may increase the size of the window 98 from 10 seconds to 30 seconds to capture more data prior to providing the waveform variability. This may provide more accurate and/or stable waveform variability values, but may also slow the updating. The monitor 22 may provide rolling updates as the window 98 moves forward in time.

Turning back to FIG. 3, one or more patient parameters may be used to adjust or correct the calculated plethysmographic waveform variability at step 70. In general, certain patient conditions may influence or have a correlative or inverse correlative relationship with the plethysmographic waveform. For example, the plethysmographic waveform variability may be particularly sensitive to vasoconstriction. In embodiments, the monitor 22 may allow a clinician to input information into the monitor related to whether or not the patient is taking any vasoconstrictive drugs, such as vasopressin analogs. Because vasoconstriction may increase cardiac preload and cardiac output, the resultant plethysmographic waveform may be adjusted to account for the effects of vasoconstrictive drugs. Similarly, certain clinical conditions may cause vasoconstriction, including stress and hypothermia. Accordingly, information from temperature sensors may provide information about whether or not vasoconstriction may be a factor in influencing the plethysmographic waveform variability. When patient parameters indicative of vasoconstriction are available, the plethysmographic waveform variability may be adjusted accordingly.

Similarly, information relating to whether or not a patient is receiving positive end expiratory pressure (PEEP) ventilation may be used to adjust the plethysmographic waveform variability. PEEP can cause significant hemodynamic consequences through decreasing venous return to the right heart and decreasing right ventricular function. PEEP may increase intrathoracic pressure, leading to a resulting decrease in venous return and decrease in cardiac output. Accordingly, information relating to PEEP may be used to adjust the plethysmographic waveform variability to a lower threshold value indicative of hypovolemia, as discussed below. For example, because PEEP and intravascular volume depletion may be contraindicated, a patient receiving PEEP may be closely monitored for hypovolemia and may have a lower plethysmograhpic waveform variability threshold. In addition, PEEP may lead to an increase in plethysmographic waveform variability, meaning that the plethysmographic waveform variability may be adjusted downwards to account for the effects of PEEP.

A patient parameter may also be used to determine if plethysmographic waveform variability is likely to be accurate for the patient in question. For example for patients with normal tidal volumes, e.g., between 8 and 15 kg/ml, the plethysmographic waveform variability value may be a generally accurate estimate of intravascular volume or fluid responsiveness. Accordingly, for these patients, the plethysmographic waveform variability value may not be adjusted when their tidal volumes are in the normal range. However, for patients outside of the range of normal tidal volumes, the plethysmographic waveform variability value may be less accurate and maybe adjusted according to its relationship with tidal volumes outside of normal ranges.

In embodiments, tissue water fraction information from an aquametry sensor 26 may be used to adjust the plethysmographic waveform variability. Because plethysmographic waveform variability may be used as a surrogate for blood volume, information about the hydration state of other compartments, such as the tissue, may provide additional information for assessing intravascular blood volume. Total body water depletion through dehydration may lead to poor intravascular volume. The body may protectively shunt blood towards the most vital organs (heart, kidney and brain) and away from peripheral organs such as the intestines, muscles and skin. Hence, the earliest sign of dehydration may be seen in the skin and muscle tissues. A reduced extracellular fluid volume, e.g., tissue water fraction, may be an early indicator of low intravascular volume. A tissue water fraction may be determined according to methods discussed in U.S. Patent Publication No. 2008/0221411 to Hausmann et al., filed on Mar. 9, 2007, the specification of which is incorporated by reference herein in its entirety for all purposes. If the tissue water fraction is associated with a low level of hydration, the plethysmographic waveform variability may be increased or adjusted upwards to reflect a higher likelihood of hypovolemia. In addition, the tissue water fraction may be used as a confirmation or confidence check for the plethysmographic waveform variability.

Further, information from a carbon dioxide sensor 24 may be used to adjust the plethysmographic waveform variability. Abnormally low levels of carbon dioxide in end tidal breaths may correlate with a concurrent decrease in blood volume. Accordingly, the plethysmographic waveform variability may be increased or adjusted upwards to reflect a higher likelihood of hypovolemia for patients with decreased end tidal carbon dioxide levels.

The monitor 22 may calculate the adjusted plethysmographic variability value and provide a display or other indication to a clinician, such as a graphical, visual, or audio representation of the intravascular volume at step 72. For example, an adjusted plethysmographic variability value associated with normal intravascular blood volume may include a numeric value or a green light indicated on a display or a short tone generated by a speaker associated with monitor 22. Similarly, an adjusted plethysmographic variability value associated with hypovolemia may trigger an alarm, which may include one or more of an audio or visual alarm indication. Further, the monitor 22 may provide a confidence metric or indicator to provide information to the clinician relating to how may parameters may have been taken into account. For example, if the plethysmographic variability value is consistent with trends from two or more additional patient parameters, the confidence may be higher than if only one patient parameter is used.

In one embodiment, the alarm may be triggered if the adjusted plethysmographic variability value is substantially greater than a predetermined value, substantially less than a predetermined value, or outside of a predetermined range. In one embodiment, a plethysmographic variability value of 10-15% may be considered to be indicative of a non-responsive or normovolemic patient that would not benefit from a fluid infusion. In addition, a plethysmographic variability value above 15% may be considered to be indicative of a hypovolemic patient that would likely benefit from a fluid infusion with respect to increasing cardiac output and improving the overall state of oxygenation. Accordingly, an alarm may be triggered when the plethysmographic waveform variability value is above 15% to alert a clinician that the patient may benefit from fluid therapy.

Figure 5:
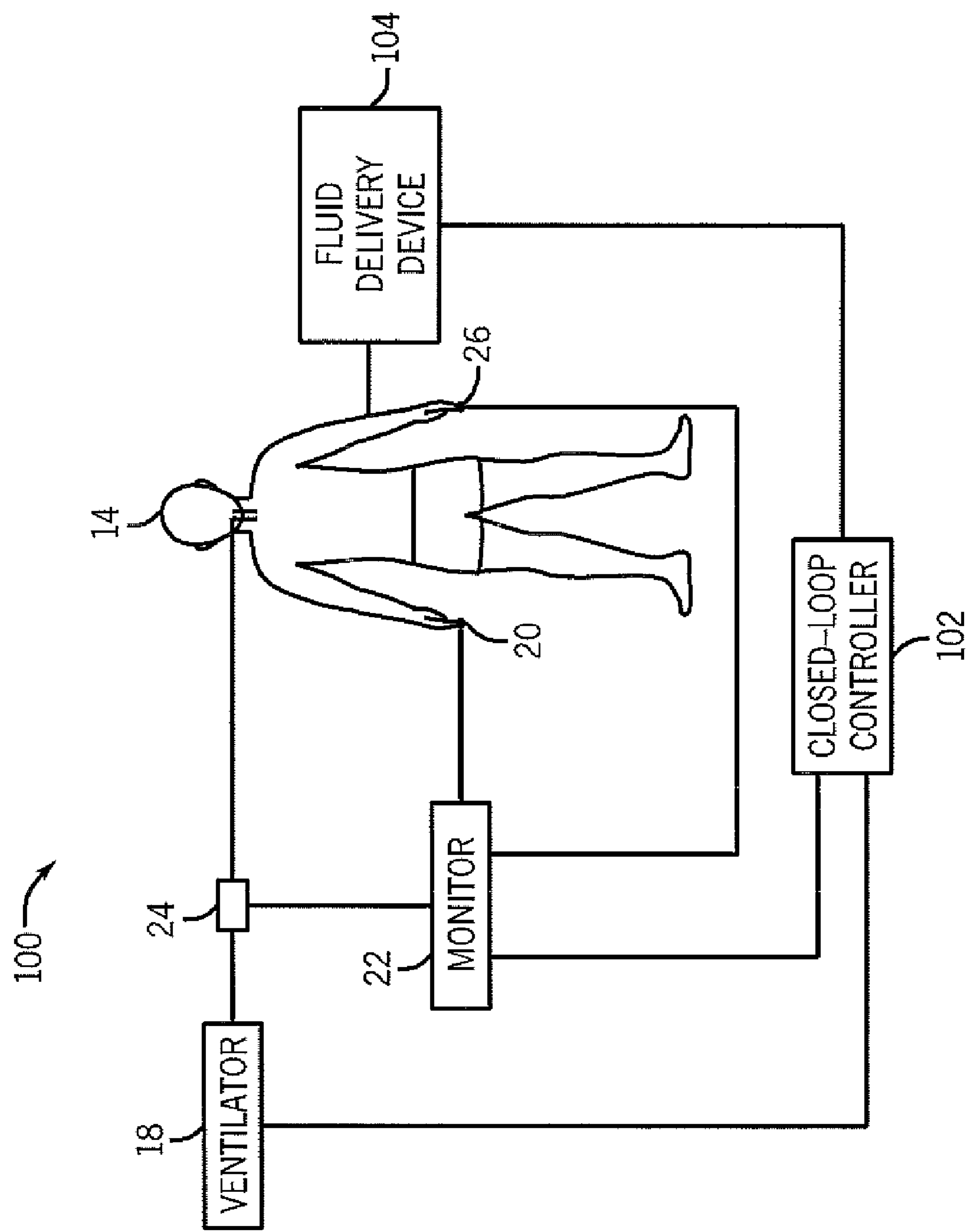
FIG. 5 is a block diagram of a closed-loop ventilation system for administering a fluid therapy in accordance with an embodiment.

In other embodiments, a patient respiratory system 100 may operate under closed-loop control to provide to delivery of a fluid therapy (e.g., saline, blood, or other fluid) to a patient 14. FIG. 5 shows a system 100 under control of a primary controller 102 that may include a closed-loop controller that cooperates with a monitor 22 to control delivery of fluid therapy to the patient 14. The primary controller 102 may receive input from the monitor 22. Based on the plethysmographic waveform signal from the pulse oximetry sensor 20 as well as additional patient parameter information, such as the settings of ventilator 18 or the inputs from additional patient sensors, the monitor 22 may calculate a plethysmographic waveform variability value. The plethysmographic waveform variability value may be used by the controller 102 to control the fluid delivery device 104. It should be understood that while FIG. 5 depicts the controller 102 and the monitor 22 as separate devices, the monitoring functions of monitor 22 and the controller functions of controller 102 may be incorporated into a single device in embodiments.

For example, the controller 102 may receive a request for increased fluid from the monitor 22 when a measured plethysmographic waveform variability value, adjusted with regard to available patient parameters, is above a predefined target, e.g., above 15%. The fluid delivery device 104 may include a peristaltic pump or other type of pump attached to an automatic intravenous line to achieve the desired delivery rate of the fluid to the patient. To control the rate at which the pump infuses the fluid, the speed of the pump may be controlled by the closed-loop controller 102. When the plethysmographic waveform variability value falls below 15%, the controller 102 may slow or stop delivery of fluid from the fluid delivery device 104. If the monitor 22 fails to determine that a plethysmographic waveform variability value has decreased after a set time, the controller 102 may generate a signal notifying a caregiver of prolonged hypovolemia or may cease delivery of fluids.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method, comprising:

using a processor:

receiving a plethysmographic waveform signal from a sensor, wherein the plethysmographic waveform signal is representative of a blood oxygen saturation of a patient;

receiving information related to a patient parameter that influences the plethysmographic waveform signal; and determining a plethysmographic waveform variability based at least in part on the plethysmographic waveform signal; and correcting the plethysmographic waveform variability to generate a corrected variability value based on the information related to the patient parameter, wherein the information related to the patient parameter comprises a tissue carbon dioxide level.

2. The method of claim 1, comprising providing an indication of intravascular blood volume based on the corrected variability value.

3. The method of claim 1, comprising triggering an alarm when the corrected variability value is greater than a predetermined level or outside of a predetermined range.

4. The method of claim 3, wherein the predetermined level is 15%.

5. The method of claim 1, wherein the information related to the patient parameter comprises a ventilator setting of positive end pressure ventilation, a tidal volume, a respiration rate, an end-tidal carbon dioxide level, or any combination thereof.

6. The method of claim 1, wherein the information related to the patient parameter comprises a clinical condition of the patient or information related to a pharmacological treatment.

7. The method of claim 6, wherein the clinical condition comprises a likelihood of vasoconstriction.

8. A monitor, comprising:

an input circuit configured to receive a plethysmographic waveform signal and information relating to a patient parameter that influences the plethysmographic waveform signal;

a memory storing an algorithm configured to calculate a corrected plethysmographic waveform variability based at least in part on the plethysmographic waveform signal and the information related to the patient parameter wherein the information relating to the patient parameter comprises information that the patient is undergoing positive end expiratory pressure ventilation, and wherein the algorithm is configured to increase the plethysmographic waveform variability based on the information; and an output circuit configured to provide an indication of the corrected plethysmographic waveform variability.

9. The monitor of claim 8, wherein the information relating to a patient parameter comprises information received from a carbon dioxide sensor or a tissue water fraction sensor.

10. The monitor of claim 8, wherein the information relating to a patient parameter comprises respiratory parameter information.

11. The monitor of claim 8, wherein the algorithm comprises the following equation:

$$W_v=(W_{max}-W_{min})/W_{mean},$$

wherein $W_v$ is the plethysmographic waveform variability, $W_{max}$ is a maximum peak value for a largest peak, $W_{min}$ is a minimum peak value for a smallest peak, and $W_{mean}$ represents the mean vertical distance between peak maxima and minima for the consecutive peaks in the window within a window of consecutive peaks.

12. The monitor of claim 8, wherein the information related to the patient parameter comprises a tidal volume, and wherein the algorithm is configured to correct the plethysmographic waveform variability when the tidal volume is outside of a range of between 8 to 15 kg/ml.

13. The monitor of claim 8, wherein the information relating to the patient parameter comprises information that the patient is receiving vasoconstrictive drugs, and wherein the algorithm is configured to adjust the plethysmographic waveform variability based on the information.

14. A method, comprising:

using a processor:

receiving a plethysmographic waveform signal from a sensor, wherein the plethysmographic waveform signal is representative of a blood oxygen saturation of a patient;

receiving information related to a patient parameter that influences the plethysmographic waveform signal; and determining a plethysmographic waveform variability based at least in part on the plethysmographic waveform signal; and correcting the plethysmographic waveform variability to generate a corrected variability value based on the information related to the patient parameter, wherein the information related to the patient parameter comprises a tissue water fraction.

15. The method of claim 14, comprising providing an indication of intravascular blood volume based on the corrected variability value.

16. The method of claim 14, comprising triggering an alarm when the corrected variability value is greater than a predetermined level or outside of a predetermined range.

17. The method of claim 16, wherein the predetermined level is 15%.

18. The method of claim 14, wherein the information related to the patient parameter comprises a ventilator setting of positive end pressure ventilation, a tidal volume, a respiration rate, an end-tidal carbon dioxide level, or any combination thereof.

* * * * *